United States Patent [19]

Gluchowski

[11] Patent Number: 4,927,846

[45] Date of Patent: May 22, 1990

[54] INTRAOCULAR PRESSURE REDUCING 1,11-LACTONE PROSTAGLANDINS

[75] Inventor: Charles Gluchowski, Mission Viejo, Calif.

[73] Assignee: Allergan, Inc., Irvine, Calif.

[21] Appl. No.: 275,465

[22] Filed: Nov. 23, 1988

[51] Int. Cl.$^5$ ............................................ A61K 31/335
[52] U.S. Cl. ...................................... 514/450; 514/913
[58] Field of Search ................ 514/557, 573, 450, 913

[56] References Cited

U.S. PATENT DOCUMENTS 4,067,991  1/1978  Bundy ................................. 514/450
4,599,353  7/1986  Bito ..................................... 514/573

Primary Examiner—Douglas W. Robinson
Assistant Examiner—Zohreh A. Fay
Attorney, Agent, or Firm—Martin A. Voet

[57] ABSTRACT

The prostaglandin 1,11-lactone $PGF_{2\alpha}$ is disclosed for lowering intraocular pressure.

4 Claims, No Drawings

INTRAOCULAR PRESSURE REDUCING 1,11-LACTONE PROSTAGLANDINS

BACKGROUND OF THE INVENTION

The present invention relates to compositions of matter for reducing or maintaining intraocular pressure, and, more particularly, to a method and composition for reducing or maintaining intraocular pressure involving the administration of a 1,11-lactone of a prostaglandin or prostaglandin analog in an opthalmically acceptable medium.

The compositions and method of the present invention are particularly useful for the management of glaucoma, a disease of the eye characterized by increased intraocular pressure. On the basis of its etiology, glaucoma has been classified as primary or secondary. For example, primary glucoma in adults, e.g., congenital glaucoma, may be either chronic open-angle, or acute or chronic angle-closure. Secondary glaucoma results from preexisting ocular diseases such as uveitis, intraocular tumor or an enlarged cataract.

The underlying causes of primary glaucoma are not yet well known. The increased intraocular tension is typically due to obstruction of aqueous humor outflow. In chronic open-angle glaucoma, the anterior chamber and its anatomic structures appear normal but drainage of the aqueous humor is impeded. In acute and chronic angle-closure glaucoma, the anterior chambe is shallow, the filtration angle is narrowed and the iris may obstruct the trabecular meshwork at the entrance of the canal of Schlemn. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and subsequently into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40, and may be asymptomatic for years before progressing to rapid loss of vision. In cases where surgery is not indicated, topical beta-adrenoceptor antagonists have traditionally been the drugs of choice for treatment.

Certain eicosanoids, particularly various prostaglandins, have been reported to possess ocular hypotensive activity. However, prostaglandin ocular hypotensives generally suffer from the disadvantage of inducing conjunctival hyperemia of varying severity and duration, smarting, and foreign body sensation as well as presenting solubility problems in certain ophthalmically advantageous carriers.

This invention relates to derivatives of the known prostaglandins formulated in a pharmaceutically acceptable vehicle, and ophthalmic used of these prostaglandins. The present invention has numerous advantages over the prior art, including increased duration of action and elimination or reduction of the aforementioned undesirable side effects, and easy solubilization in certain ophthalmically advantageous carriers.

SUMMARY OF THE INVENTION

In accordance with one aspect of the present invention, there is provided a method of treating ocular hypertension which comprises applying to the eye an amount sufficient to treat ocular hypertension of a 1,11-lactone of PGF or its analogs, the compounds of formula I or II.

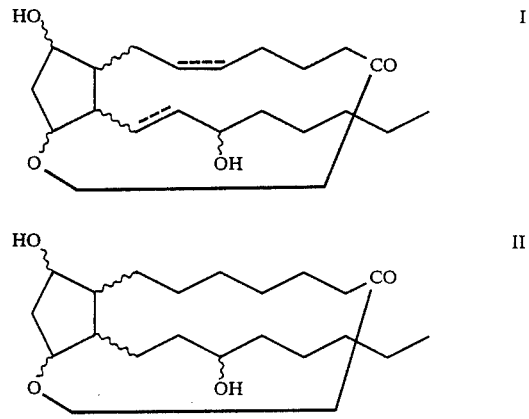

In accordance with a further aspect of the present invention, there is provided a composition for treating ocular hypertension, which comprises one or more of the 1,11-lactones as described above, together with an ophthalmically acceptable excipient.

Further features and advantages of the present invention will become apparent from the detailed description of preferred embodiments which follows, taken together with the examples and claims appended hereto.

DETAILED DESCRIPTION OF PREFERRED EMBODIMENTS

In the foregoing illustration, as well as those provided hereinafter, wavy line attachments indicate either the alpha or beta configuration. The dotted lines on bonds of C-5 and C-13 indicate a double bond which can be in the cis or trans configuration. If two solids lines are used at C-5 or C-13, that indicates a specific configuration for that double bond. Hatched lines used at position C-9, C-11 and C-15 indicate the alpha configuration. If one were to draw the beta configuration, a solid triangular line would be used at either of these three positions.

$PGF_{2\alpha}$ is known to exist in certain mammalian tissues such as, for example, human seminal plasma and sheep vesicular glands, and pure $PGF_{2\alpha}$ obtained from these tissues is commercially available from the Sigma Chemical Company.

It has been discovered that certain prostaglandins lower intraocular pressure in man and other mammals when applied topically to the cornea. Although the precise mechanism is not yet known, prostaglandins appear to increase aqueous humor outflow to restore a normotensive or hypotensive state. However, topical application of prostaglandins generally causes side effects such as conjunctival hyperemia, smarting and foreign body sensations which range in degree from undesirable to unacceptable, depending upon the particular patient and dosage necessary to produce a sufficient pressure regulating effect.

In accordance with one aspect of the present invention, there has been provided a method for treating ocular hypertension which comprises administering to the eye a 1,11-lactone of PGF (formula I) of a 1,11-lactone of a PGF analog where the C-5 and C-13 bonds are saturated (formula II). It has further been discovered that these lactones are more effective than $PGF_{2\alpha}$ both in terms of degree and duration of activity. In addition, animals treated with formulations comprisig these 1,11-lactones experience significantly reduced adverse side effects. These lactones are further advantageous as a result of their increased solubility in certain therapeutically acceptable eye drop vehicles, such as 0.1% polysorbate 80/TRIS.

These derivatives, therefore, are excellent candidates for therapeutic treatment of the variety of ocular hypertensive conditions such as open-angle glaucoma closed-angle glaucoma, ocular hypertensive episodes, post-surgical and post-laser trabeculectomy, and as a pre-surgical adjuvant.

Preparation of the lactones for use with the present invention may be accomplished by methods known in the art, as will become apparent from the Examples which follow. For example, acceptable synthetic routes are disclosed in U.S. Pat. No. 4,067,991 to Bundy, the disclosure of which is incorporated herein by reference.

The naturally occurring stereochemistry of $PGF_{2\alpha}$ includes 9, 11 and 15 position hydroxyl groups in the alpha position. But the 9, 11 and 15 hydroxyl groups can exist in any combination of an alpha or beta configuration. While the naturally occuring configuration of $PGF_{2\alpha}$ is preferred in the practice of this invention, any of the alpha or beta configurations possible can be used in the practice of this invention. Furthermore, lactones where the C-5 double bond has the trans configuration can be used in this invention. Also, the C-13 double bond may be in the cis as well as the trans configuration, the trans being the naturally existing form. The lactones of this invention also include those compounds where C-5 and/or C-13 are saturated, as illustrated by Formula II. In each of these C-5 and C-13 configurations, the C-9, C-11 or C-15 group may be in either the alpha or beta configuration, without limit as to any particular combination of such configurations.

The preferred compounds of this invention are those having the stereochemistry of the following formula.

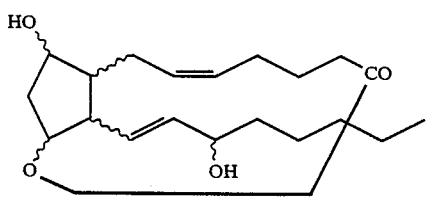

The most preferred compound of this invention is the 1,11-lactone of $PGF_{2\alpha}$ which has the following formula.

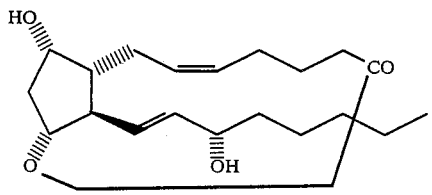

In accordance with another aspect of the present invention, an intraocular pressure reducing composition is prepared with the foregoing 1,11-lactone. The composition may comprise any of a variety of pharmaceutically acceptable carriers as will be known to those of skill in the art, depending upon the desired mode of administration. For intraocular pressure maintenance or reduction, a preferred method of application is topical, in a pharmaceutically acceptable ocular carrier such as any of a variety of drops, creams, or gels known in the art. Such a carrier may also comprise pharmaceutically required or advantageous adjuvants, along with an effective dose of the intraocular pressure reducing drug.

The actual formulation of pharmaceutical compositions incorporating the 1,11-lactone is within the skill in the art, and depends upon numerous application specific parameters such as mode of administration, desired frequency of administration, balancing of strength versus occurrence of side effects, among others. It is anticipated that the formulation for any given application will optimally include a certain amount of routine experimentation to optimize concentrations of ingredients and carriers.

In accordance with a preferred embodiment of the present invention, the carrier comprises a solution having polysorbate 80-10 mM TRIS in the range of from about 0.05-1.0% by weight, and preferably about 0.1%, which is particularly suited for administration in the form of a liquid eye drop. This carrier may additionally comprise pharmaceutically advantageous adjuvants such as a preservative, antibiotic/antimycotic agents, pH buffers or osmotic balancers.

The optimal concentration of the prostaglandin derivative is a function of a variety of factors, as has been discussed. In general, however, concentrations are contemplated within the rane of from about 0.0001% to 10%, preferably from 0.001% to 1%; and most preferably from 0.01% to 0.1% by weight in relation to the pharmaceutically acceptable carrier.

The lactonization reaction for producing the foregoing 1,11-lactone will be fully appreciated by one of skill in the art, particularly in view of the Examples which follow.

EXAMPLE I

Preparation of PGD$_2$9,15-bis(triphenylsilyl ether)

A stirred 0° C. solution of 1 g of PGD$_2$ in 25 ml of anhydrous pyridine was treated with 3 g of triphenylsilyl chloride (added in one portion), and the resulting mixture was stirred for 6 hours at 25°, diluted with 100 ml of cold tetrahydrofuran (THF) and 40 ml of cold water, and stirred 45 minutes longer at 0° C. The mixture was poured into brine, acidified (325 ml of cold 1M NaHSO$_4$), and extracted immediately with 1:1 ethyl acetate/hexane. The combined extracts were washed with brine, dried over anhydrous Na$_{2l}$ $_{SO4}$, and concentrated. The crude product was chromatographed on a 300-g column of Mallinkrodt CC-4 acid-washed silica gel, packed with 10% ethyl acetate/hexane and eluted (50 ml fractions) with 700 ml of the same solvent, followed by 2000 ml of 20% ethyl acetate/hexane. Fractions 45–67 afforded the title compound.

IR (neat) 3300, 3100, 2700, 1750, 1720, 1600, 1490, 1430, 1240, 1120, 1045, 1000, 970, 740, 710, 700 cm$^{-1}$.

NMR (CDCl$_3$) $\delta$10.75 (s, 1H, exchangeable), 7.90–7.20 (m, 30H), 5.75–5.05 (m, 4H), 4.75–4.15 (m, 2H).

EXAMPLE II

Preparation of PGF$_{2\alpha}$9,15-bis(triphenylsilyl ether)

Sodium borohydride, 3 g, in 100 mg portions over 15 minutes, was added to a stirred 0° C. solution of 4.10 g of the PGD$_2$9,15-bis(triphenylsilyl ether) from Example I in 250 ml of CH$_3$OH. After 15 additional mininutes at 0° C., the reaction mixture was carefully poured into a rapidly stirred mixture of ice, water, dilute NaHSO$_4$, 1:1 ethyl acetate/hexane. After separation of the phases, the aqueous phase was extracted with more 1:1 ethyl acetate/hexane. The extracts were washed with brine, dried (Na$_2$SO$_4$), and evaporated, and the crude product was chromatographed on silica gel. The column was packed with 10% ethyl acetate/hexane and eluted (1×800 ml, then 19 ml fractions) with 20% ethyl acetate/hexane. Fractions 40–75 yielded the PGF$_{2\alpha}$9,15-bis(triphenylsilyl ether).

EXAMPLE III

Preparation of PGF$_{2\alpha}$9,15-disilyl-1,11-lactone

A solution of 2.90 g (3.33 mmol) of PGF$_{2\alpha}$9,15-bis(triphenylsilyl ether), 1.10 g (5 mmol) of 2,2'-dipyridyl disulfide, and 1.31 g (5 mmol) of triphenylphosphine in 40 ml of dry, oxygen-free xylene was stirred at 25° C. under nitrogen for 10 hours. The mixture was then diluted with 800 ml of xylene and heated at reflux for 24 hours. After the mixture was cooled, the xylene was removed in vacuo and the dark residue was chromatographed on 450 g of silica gel. The column was packed and eluted with benzene (1×200 ml, then 50 ml fractions). Fractions 30–48 afforded of the PGF$_{2\alpha}$9,15-disilyl-1,11-lactone.

IR: 1730 cm$^{-1}$.

EXAMPLE IV

Preparation of PGF$_{2\alpha}$1,11-lactone

A mixture of 2.2 g of PGF$_{2\alpha}$9,15-disilyl-1,11-lactone, 100 ml of THF, 80 ml of water, and 20 ml of 85% H$_3$PO$_4$ was heated at 45° C. for 2 hours. The reaction mixture was then concentrated to about one-half of the original volume, diluted with water, and extracted with 3:1 ethyl acetate/hexane. The extracts were washed with aqueous NaHCO$_3$ and brine, dried (MgSO$_4$) and concentrated. The crude product was chromatographed on a 125-g column of silica gel, packed with 25% ethyl acetate/hexane and eluted (14 ml of fractions) with 800 ml of 40%, 800 ml of 55%, and 1000 ml of 70% ethyl acetate/hexane. Appropriate fractions were collected and the solvent removed to give the PGF$_{2\alpha}$1,11-lactone as a viscous, colorless oil.

IR (neat): 3400, 1730, 1710, 1450, 1350, 1335, 1270, 1225, 1185, 1145 1100, 1085, 1005, 965, 705 cm$^{-1}$.

NMR (CDCl$_3$): $\delta$5.8–4.95 (m, 5H), 4.85–4.35 m, 2H), 4.20–3.85 (m, 1H), 1.65 (s, 2H, exchangeable);

MS m/e (Me$_3$Si derivative): 480.3073 (calcd for C$_{26}$H$_{48}$Si$_2$O$_4$, M$^+$, 480.3091), 465, 390, 375, 319, 199.

EXAMPLE V

Intraocular Pressure Reducing Effect in Rabbits

Experimental quantities of the 1,11 lactone of PGF$_{2\alpha}$ were prepared in accordance with the procedure of the foregoing Examples. The resulting PGF$_{2\alpha}$1,11-lactone was added to a polysorbate carrier in amounts to produce a 0.1% solution of each lactone. A group of 8 rabbits was treated by administering approximately 1 drop of each solution to the surface of the eye, and intraocular pressure was measured by applanation pneumatonometry (Model 30RT manufactured by Digilab) at the time of administration and various time intervals thereafter. The following data were obtained:

| INTRAOCULAR PRESSURE CHANGES (mm Hg) AT PREDETERMINED TIMES (HR) AFTER PROSTAGLANDIN ADMINISTRATION | | | | | | | |
|---|---|---|---|---|---|---|---|
| | PG Dose % | | | | | | |
| | 0 | 2 | 3 | 4 | 6 | 8 | 10 |
| PGF$_{2\alpha}$ 0.1% | 0 | −2.5 | −6.1** | −3.9 | −2.2** | −1.1 | −0.8 |
| % Hyperemic 1,11-Lactone | — | 100 | 100 | 100 | 75 | 0 | 0 |
| PGF$_{2\alpha}$ 0.1% | 0 | −1.2 | −6.3** | −5.8** | −7.1** | −4.8 | −4.1 |
| % Hyperemic | — | 100 | 100 | 100 | 75 | 62.5 | 37.5 |

*p < 0.05
**p < 0.01
n = 8

Comparison of the effect of 1,11-lactone PGF$_{2\alpha}$ with the parent compound (PGF$_{2\alpha}$) on intraocular pressure revealed a marked increase in duration of activity. Thus, comparing 1,11-lactone PGF$_{2\alpha}$ and PGF$_{2\alpha}$ at a 0.1% dose, 1,11-lactone PGF$_{2\alpha}$ significantly reduced intraocular pressure again for at least about ten hours, whereas PGF$_{2\alpha}$ was significantly effective for only about six hours. PGF$_{2\alpha}$, the 1,11-lactone, also appeared advantageous in that the incidence of hyperemia associated with significant decreases in intraocular pressure was reduced relative to that observed for PGF$_{2\alpha}$.

Although this invention has been described in terms of certain preferred embodiments, other embodiments that are apparent to those of skill in the art are also within the scope of this invention. Accordingly, the scope of the invention is intended to be defined only by reference to the appended claims.

What is claimed is:

1. A method of treating ocular hypertension which comprises topically administering to the eye an intraocular pressure treating amount of a 1,11-lactone of PGF$_{2\alpha}$, the compound having the following formula:

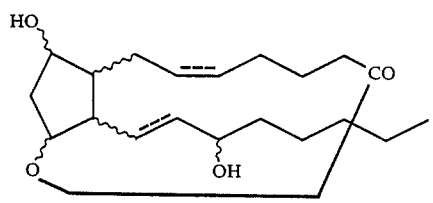

2. The method of claim 1 where the C-5 and C-9 double bonds are cis and trans respectively, the compound having the following formula:

3. The method of claim 2 where the 9, 11 and 15 groups are in the α position, the 1,11-lactone of PGF$_{2α}$, graphically represented by the following compound:

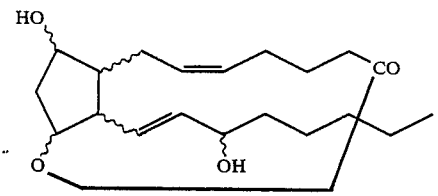

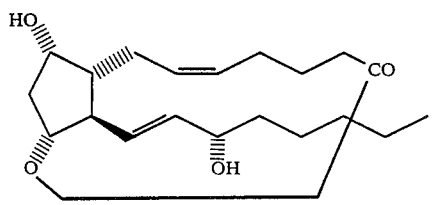

4. A method for treating ocular hypertension which comprises topically administering to the eye an amount effective to treat ocular hypertension of a 1,11-lactone of a PGF analog where the C-5 and C-13 bonds are saturated, the compound having the following formula:

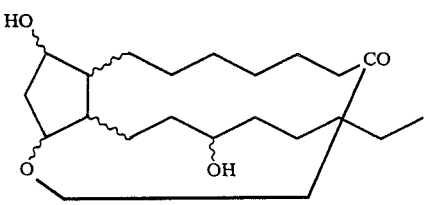

* * * * *